United States Patent
Ohtsuka et al.

(10) Patent No.: US 7,375,363 B2
(45) Date of Patent: May 20, 2008

(54) IMAGE FORMING APPARATUS AND METHOD OF TRANSPORTING SAME

(75) Inventors: Yuzuru Ohtsuka, Minami-ashigara (JP); Yasunori Ohta, Hadano (JP)

(73) Assignee: FUJIFILM Corporation, Tokyo (JP)

(*) Notice: Subject to any disclaimer, the term of this patent is extended or adjusted under 35 U.S.C. 154(b) by 228 days.

(21) Appl. No.: 11/052,522

(22) Filed: Feb. 8, 2005

(65) Prior Publication Data
US 2005/0178987 A1 Aug. 18, 2005

(30) Foreign Application Priority Data
Feb. 16, 2004 (JP) ............... 2004-038743

(51) Int. Cl.
*G01N 23/04* (2006.01)
(52) U.S. Cl. .................................... 250/582
(58) Field of Classification Search ........... 250/580, 250/581, 582
See application file for complete search history.

(56) References Cited

U.S. PATENT DOCUMENTS

| 4,694,481 A | * | 9/1987 | Tashjian et al. ............ 378/198 |
| 4,727,564 A | * | 2/1988 | Mekker et al. ............. 378/197 |
| 4,816,676 A | * | 3/1989 | Aagano ...................... 250/582 |
| 4,839,914 A | * | 6/1989 | Curry ........................... 378/61 |
| 5,045,698 A | * | 9/1991 | Kurashima .................. 250/590 |
| 5,097,497 A | * | 3/1992 | Deucher et al. ............ 378/204 |
| 6,481,887 B1 | | 11/2002 | Mirabella |
| 6,625,252 B2 | * | 9/2003 | Mirabella .................... 378/102 |
| 6,754,306 B2 | * | 6/2004 | Cho et al. ................... 378/102 |
| 2001/0053203 A1 | * | 12/2001 | Ishii et al. .................. 378/198 |

FOREIGN PATENT DOCUMENTS

| JP | 10-246999 A | 9/1998 |
| JP | 2001-299743 A | 10/2001 |

\* cited by examiner

*Primary Examiner*—David Porta
*Assistant Examiner*—Mark R Gaworecki
(74) *Attorney, Agent, or Firm*—Sughrue Mion, PLLC

(57) ABSTRACT

After a main unit has captured an image of a subject, the main unit is detached from a support post fixedly mounted in a compartment of a vehicle through a mounting/dismounting mechanism, and stored in a storage case disposed in the compartment of the vehicle. The storage case, which can be closed by a lid, incorporates therein first and second thermal insulating members made of a thermal insulating material, and first and second damping members disposed respectively in the first and second thermal insulating members for absorbing vibrations from the vehicle.

13 Claims, 9 Drawing Sheets

IMAGE FORMING APPARATUS AND METHOD OF TRANSPORTING SAME

BACKGROUND OF THE INVENTION

1. Field of the Invention

The present invention relates to an image forming apparatus for being mounted on a vehicle, and more particularly to an image forming apparatus having an exposure unit detachably installed on a mount fixedly supported on a vehicle for transporting the exposure unit, and a method of transporting such an image forming apparatus.

2. Description of the Related Art

There have heretofore been known image forming apparatus for recording radiation image information of a subject such as a human body on a stimulable phosphor sheet having a stimulable phosphor layer. A stimulable phosphor is a phosphor which, when exposed to an applied radiation (X-rays, α-rays, β-rays, γ-rays, electron beams, ultraviolet radiation, or the like), stores part of the energy of the radiation, and, when subsequently exposed to applied stimulating rays such as visible light, emits photostimulated luminescence in proportion to the stored energy of the radiation.

An image forming apparatus disclosed in Japanese Laid-Open Patent Publication No. 2001-299743 is installed on a vehicle such as a mobile medical examination car and mounted on the chassis of the mobile medical examination car. The disclosed image forming apparatus can take pictures of subjects for medical examination within the vehicle and at remote sites.

Generally, image forming apparatus for use on vehicles have optical systems that are subject to vibrations. For example, Japanese Laid-Open Patent Publication No. 2001-299743 discloses an image forming apparatus comprising a medical image scanner for scanning patient's bodies. When the image forming apparatus is installed on a vehicle, the optical system thereof is subject to vibrations from the wheels of the vehicle while the vehicle is being driven or vibrations from the engine or electric generator on the vehicle, and may tend to decrease in function.

Heretofore, the image forming apparatus for use on vehicles have not been equipped with a vibration suppressing mechanism for blocking vibrations from being applied from the vehicle to the optical system. Consequently, since the optical system decreases more in function as the resolution of the image forming unit of the image forming apparatus for reading images is higher, it has been difficult to install highly accurate image forming apparatus on vehicles.

Japanese Laid-Open Patent Publication No. 10-246999 discloses a structure for fixing an image forming apparatus to a floor to prevent it from falling by an engaging member mounted on a plate disposed on the floor and held in engagement with a plurality of engaged members on a lower portion of the image forming apparatus.

However, Japanese Laid-Open Patent Publication No. 2001-299743 and Japanese Laid-Open Patent Publication No. 10-246999 disclose or suggest nothing about a vibration suppressing mechanism for blocking vibrations from being applied from the vehicle to the optical system mounted on the vehicle.

Consequently, the optical system of the disclosed image forming apparatus is liable to decrease in function due to vibrations that are directly applied to the optical system while the vehicle is being driven.

SUMMARY OF THE INVENTION

It is a general object of the present invention to provide an image forming apparatus having an exposure unit detachably installed on a mount fixedly supported on a vehicle for protecting the exposure unit from vibrations from the vehicle and for transporting the exposure unit, and a method of transporting such an image forming apparatus.

According to the present invention, an image forming apparatus for being carried in a compartment of a vehicle such as a mobile medical examination car or the like has an exposure unit for capturing an image of a subject, the exposure unit being detachably installable on a mount fixedly disposed in the compartment of the vehicle through a mounting/dismounting mechanism. When the vehicle which is carrying the image forming apparatus is to be driven, the exposure unit is removed from the mount, so that vibrations applied from the vehicle to the mount will not be imposed on the exposure unit. The exposure unit which is susceptible to vibrations is thus protected against undue vibrations while the vehicle is in motion. The image forming apparatus with the exposure unit, which has a high-precision optical system, can therefore be carried on the vehicle.

When the vehicle stops and the exposure unit is to capture an image of a subject, the exposure unit is installed on the mount again through the mounting/dismounting mechanism. With the exposure unit installed on the mount, the image forming apparatus can perform an image forming process on the subject as usual.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
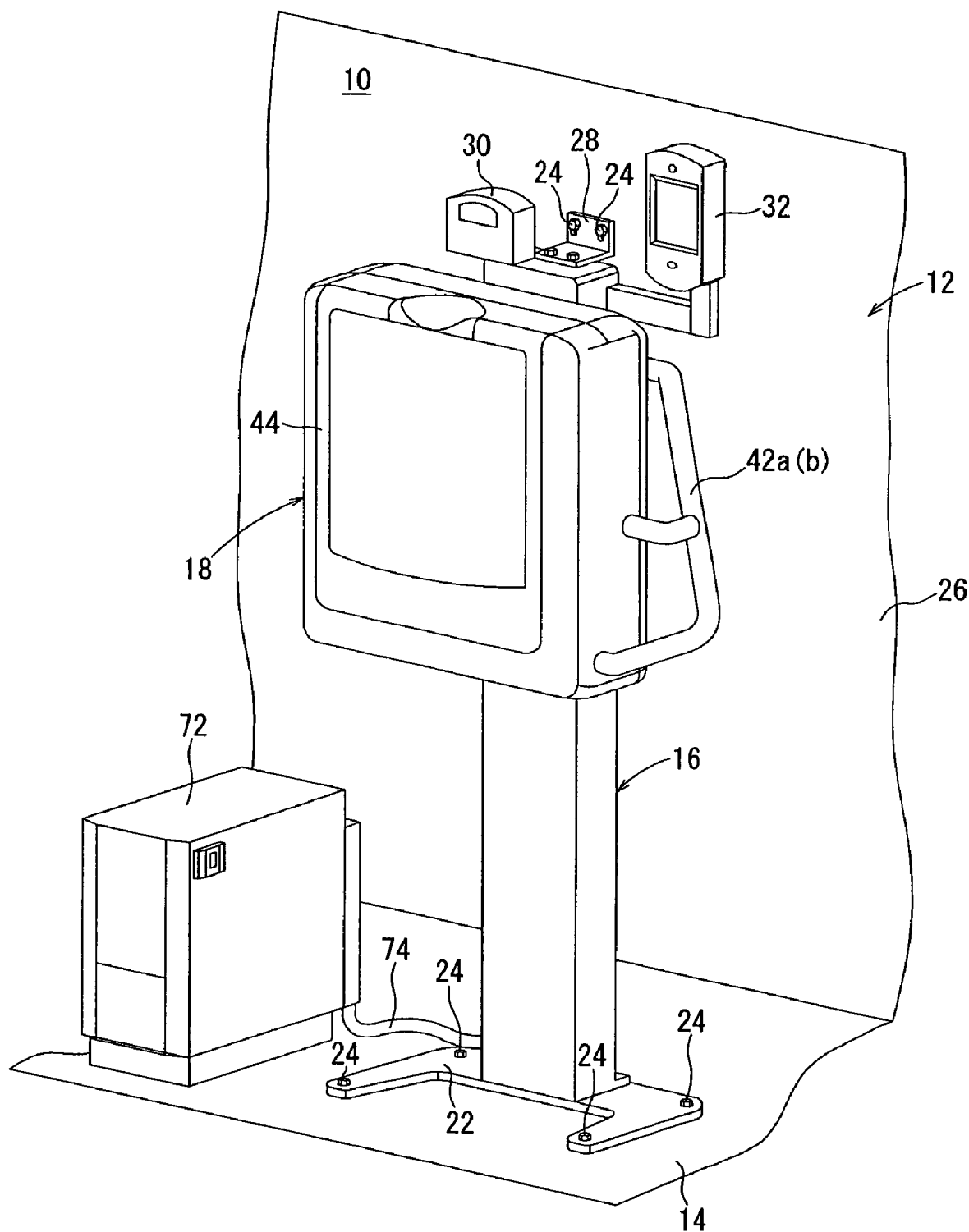
FIG. 1 is a fragmentary perspective view showing an image forming apparatus according to an embodiment of the present invention, which is installed in a compartment of a vehicle.

FIG. 1 shows in fragmentary perspective an image forming apparatus 10 according to an embodiment of the present invention, which is installed in a compartment of a vehicle.

As shown in FIG. 1, the image forming apparatus 10 has a support post (mount) 16 erected on a floor 14 of a vehicle 12 (see FIG. 9) such as a mobile medical examination car for performing medical examination therein, a main unit (exposure unit) 18 supported on the support post 16 for vertical movement along its vertical axis, and a mounting/dismounting mechanism 20 (see FIG. 2) disposed on the main unit 18 for removably installing the main unit 18 on the support post 16.

The support post 16 has a substantially rectangular horizontal cross section and includes a plate-like support base 22 disposed on the lower end thereof and lying substantially perpendicularly to the axis of the support post 16. The support base 22 is fastened to the floor 14 in the compartment of the vehicle 12 by mounting bolts 24.

A fixing bracket 28 is mounted on the upper end of the support post 16 in facing relation to a wall 26 of the vehicle 12 which extends substantially perpendicularly to the floor 14. The support post 16 is secured to the wall 26 by the fixing bracket 28 which is fastened to the wall 26 by the mounting bolts 24. Therefore, the support post 16 is firmly mounted in the compartment of the vehicle 12 by at least two members, i.e., the support base 22 and the fixing bracket 28.

A display unit 30 and a console panel 32 are also mounted on the upper end of the support post 16. The display unit 30 has a function to display instructions for capturing an image of a patient as a subject 34 (see FIG. 2). The console panel 32 is operated by the operator to activate the image forming apparatus 10, and has a function to display patient information, an exposure size, selectable items, and utility control information.

Figure 2:
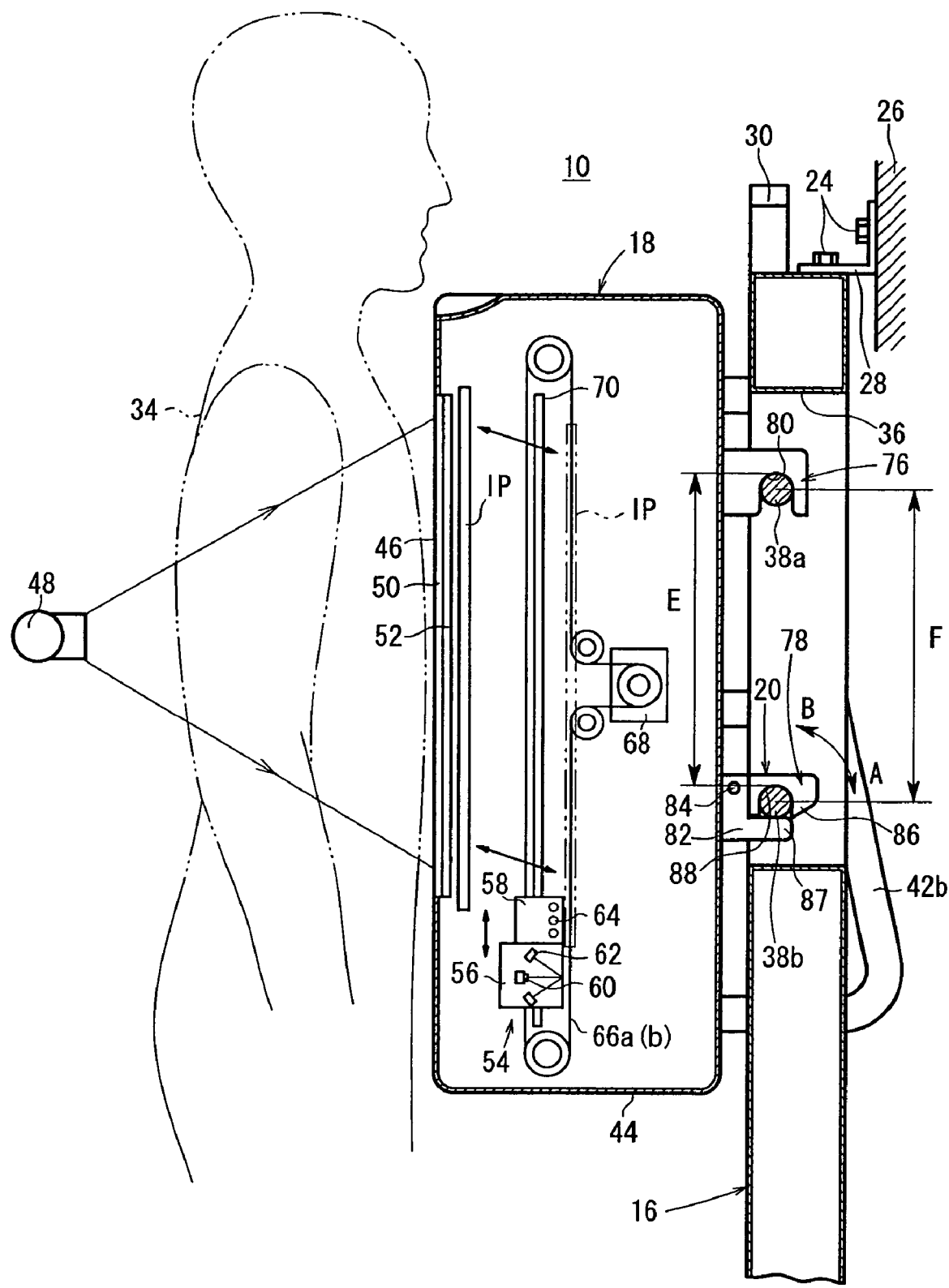
FIG. 2 is a fragmentary vertical cross-sectional view of a main unit and other components of the image forming apparatus shown in FIG. 1.
Figure 3:
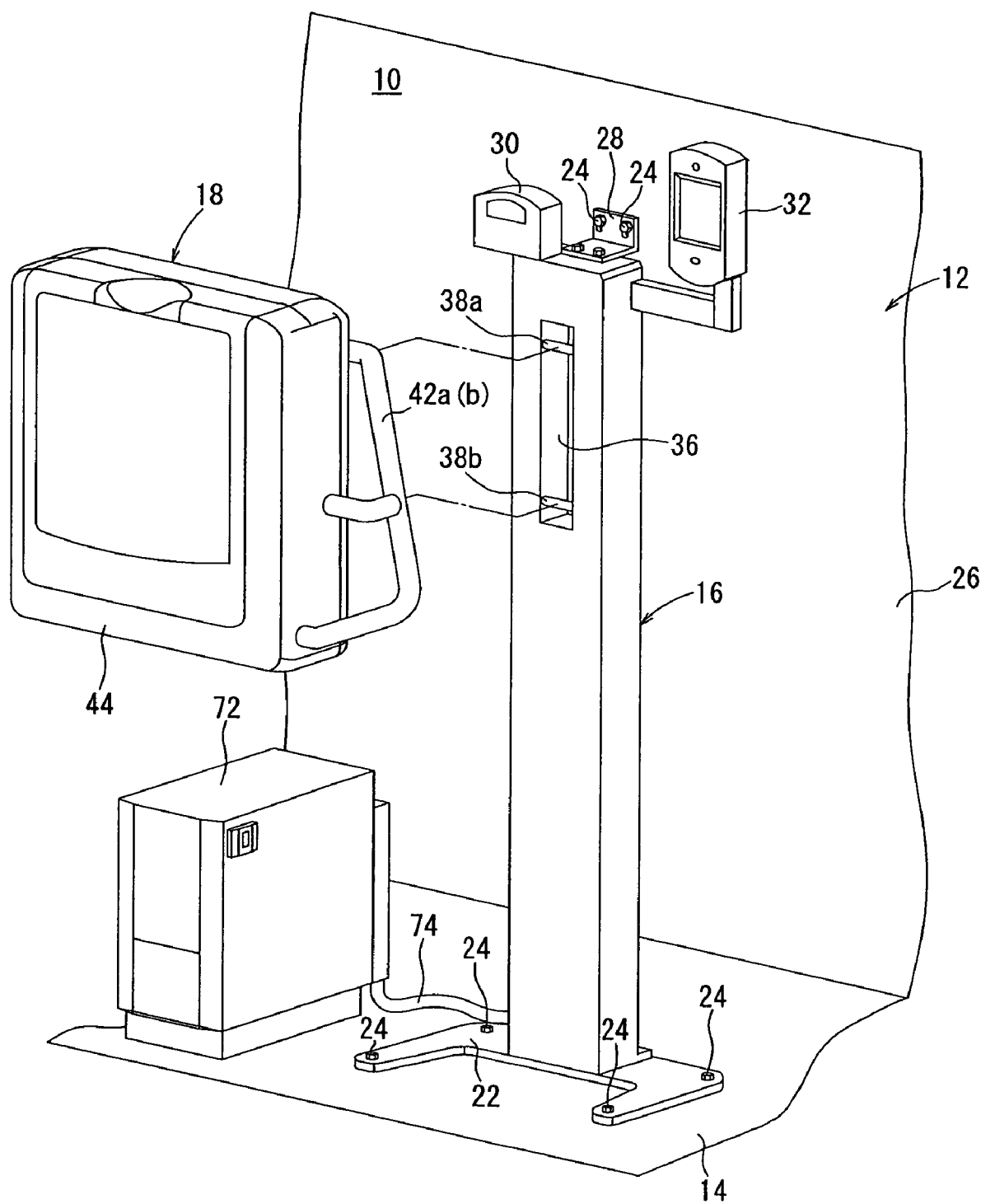
FIG. 3 is an exploded perspective view of the image forming apparatus shown in FIG. 1, with the main unit detached from a support post.

As shown in FIG. 3, the support post 16 has a mounting hole 36 defined in a side panel thereof which faces the main unit 18 where the main unit 18 is installed on the support post 16. The mounting hole 36 is of a rectangular shape that is elongate along the axis of the support post 16, and passes through the support post 16 in a direction approximately perpendicular to the axis of the support post 16 (see FIG. 2). Further, the mounting hole 36 houses therein a pair of shafts (first and second engaging elements) 38a, 38b (see also FIG. 2) extending substantially perpendicularly to the axis of the support post 16. The shafts 38a, 38b are vertically spaced from each other.

The main unit 18 has a pair of grip bars 42a, 42b (see FIG. 7) mounted on its opposite sides for the subject 34 (see FIG. 2) to grip to keep its posture for capturing its image. As shown in FIG. 2, the main unit 18 has a box-shaped housing 44 including a front panel serving as an exposure base 46 for positioning the subject 34 thereon. The exposure base 46 is combined with a phototimer 50 for measuring a dose of X-rays applied from a radiation source 48 through the subject 34 to control the amount of radiation to be applied, and a grid 52 for removing scattered rays.

The main unit 18 accommodates therein a stimulable phosphor sheet IP that is movable between a position (indicated by the solid lines) close to the grid 52 and a position (indicated by the two-dot-and-dash lines) remote from the grid 52.

The main unit 18 also houses therein a reading/erasing unit 54 that is vertically movable along the front surface of the stimulable phosphor sheet IP which is in the position indicated by the two-dot-and-dash lines. The reading/erasing unit 54 comprises a reader 56 for applying stimulating light to the stimulable phosphor sheet IP and photoelectrically reading photostimulated luminescence emitted from the stimulable phosphor sheet IP depending on the intensity of radiation energy stored in the stimulable phosphor sheet IP as representing radiation image information, and an eraser 58 for applying erasing light to the stimulable phosphor sheet IP from which the radiation image information has been read to remove any radiation energy from the stimulable phosphor sheet IP.

The reader 56 comprises a plurality of light sources 60 each having a laser diode for emitting stimulating light, and a plurality of CCD line sensors 62 for converting the photostimulated luminescence emitted from the stimulable phosphor sheet IP into an electric signal. The eraser 58 comprises a plurality of light sources 64 for emitting erasing light.

The reading/erasing unit 54 is connected to feed belts 66a, 66b which are driven by a reading/erasing unit moving motor 68 to move the reading/erasing unit 54 vertically along guide rails 70 which extend vertically on both sides of the stimulable phosphor sheet IP.

The mounting/dismounting mechanism 20 is mounted on a side panel of the housing 44 of the main unit 18 which faces the support post 16.

The mounting/dismounting mechanism 20 comprises a first hook (first engaging member) 76 projecting a predetermined distance from the side panel of the housing 44 toward the support post 16, and a second hook (second engaging member) 78 projecting a predetermined distance from the side panel of the housing 44 toward the support post 16 and spaced a predetermined distance downwardly from the first hook 76 in a vertical axial direction of the main unit 18. The first hook 76 and the second hook 78 are disposed in line in the axial direction of the main unit 18 on the side panel of the housing 44 (see FIG. 7), and project substantially the same distance from the side panel of the housing 44.

Figure 7:
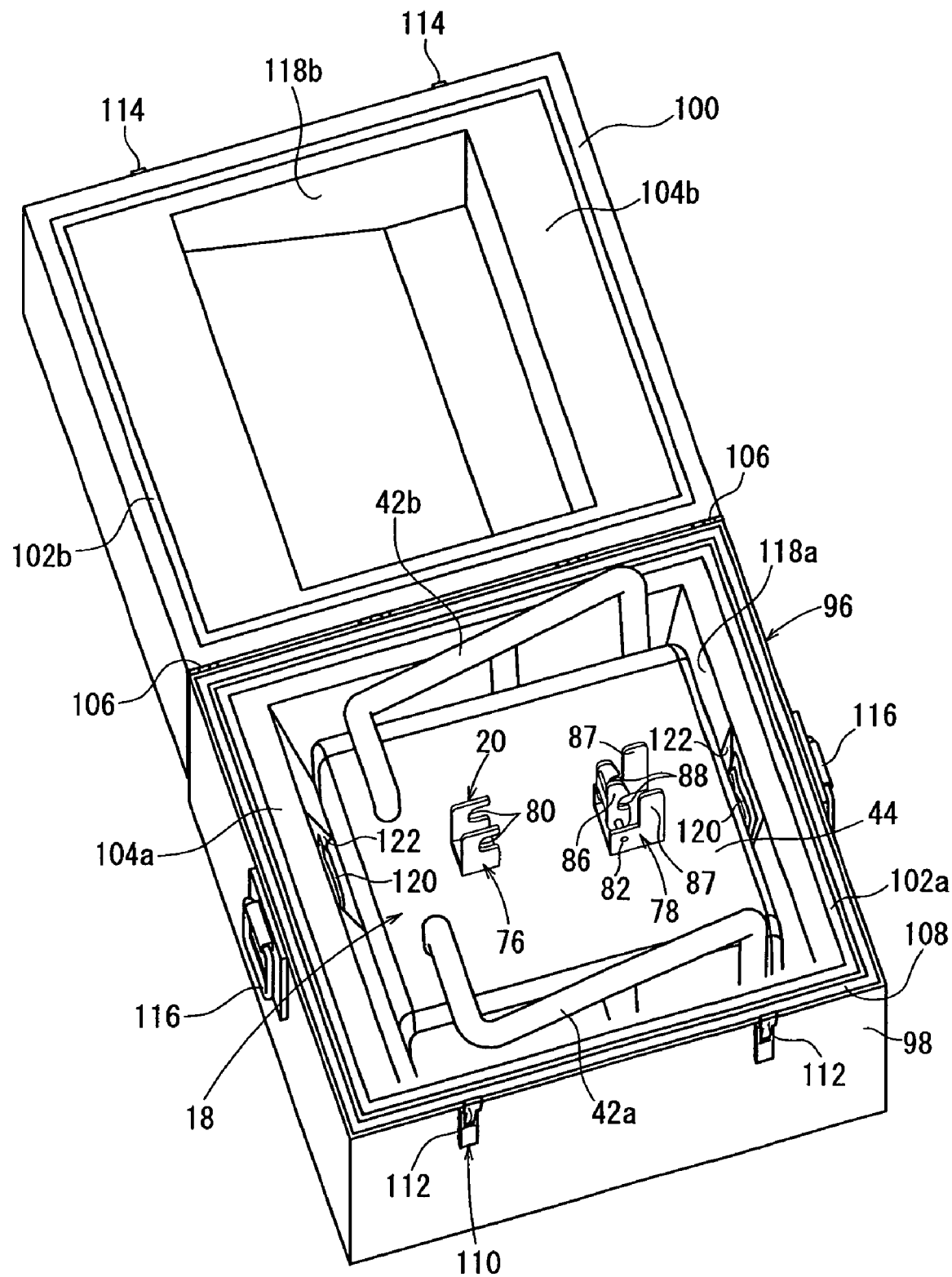
FIG. 7 is a perspective view of a storage case which stores therein the main unit detached from the support post.

The first hook 76 has a pair of first engaging grooves 80 which are of a semicircular or U shape opening downwardly (see also FIG. 7).

The second hook 78 comprises a pair of holders 82 mounted on the side panel of the housing 44, a pair of turn arms 86 angularly movably supported on the holders 82 by a pin 84, and a spring (not shown) interposed between the holders 82 and the turn arms 86. The turn arms 86 are normally biased to move in a direction indicated by the arrow A which is substantially perpendicular to the side panel of the housing 44, under the resiliency of the spring.

As shown in FIG. 2, each of the holders 82 is substantially L-shaped and has a finger 87 positioned downwardly of the corresponding turn arm 86 and spaced a given distance from the turn arm 86. The finger 87 projects substantially perpendicularly away from the side panel of the housing 44.

The finger 87 projects to a position covering a lower portion of the shaft 38b in the support post 16 when the turn arm 86 engages the shaft 38b. The finger 87 which is disposed on a lower portion of the holder 82 is effective to prevent the main unit 18 from being displaced upwardly when the main unit 18 is fixed to the support post 16 by the turn arm 86. Therefore, when an image of the subject 34 is to be captured while the main unit 18 is being secured to the support post 16, the image can stably be captured as the main unit 18 is not displaced upwardly with respect to the support post 16.

Each of the turn arms 86 has a second engaging groove 88 which is of a semicircular or U shape opening downwardly, as with the first hook 76. The U-shaped first and second engaging grooves 80, 88 have a width which is substantially the same as or slightly greater than the diameter of the shafts 38a, 38b in the support post 16. The first engaging groove 80 in the first hook 76 and the second engaging groove 88 in the second hook 78 are vertically spaced from each other by a distance E (see FIG. 2) which is substantially the same as a distance F (see FIG. 2) between the axes of the shafts 38a, 38b (E≈F).

When each turn arm 86 is angularly moved in the direction indicated by the arrow A under the resiliency of the spring, the turn arm 86 is prevented by the holder 82 from being angularly displaced downwardly beyond a position where the turn arm 86 extends substantially perpendicularly to the side panel of the housing 44. Therefore, the turn arm 86 is angularly movable in an angular range of about 90° between the position where the turn arm 86 extends substantially perpendicularly to the side panel of the housing 44 and a position where the upper surface of the turn arm 86 lies substantially parallel to the side panel of the housing 44.

Each turn arm 86 has a slanted surface 89 which is slanted at a certain angle on a lower surface thereof between the second engaging groove 88 and the distal end of the turn arm 86. The slanted surface 89 is slanted progressively upwardly in a direction away from the second engaging groove 88.

As shown in FIG. 1, a controller 72 for controlling the image forming apparatus 10 is disposed outside of the main unit 18. The controller 72 is connected to a connector (not shown) of the main unit 18 by a cable 74. The cable 74 is detachably connected to the connector of the main unit 18. For dismounting the main unit 18 from the support post 16, the cable 74 is disconnected from the connector. For mounting the main unit 18 on the support post 16, the cable 74 is connected to the connector.

Figure 9:
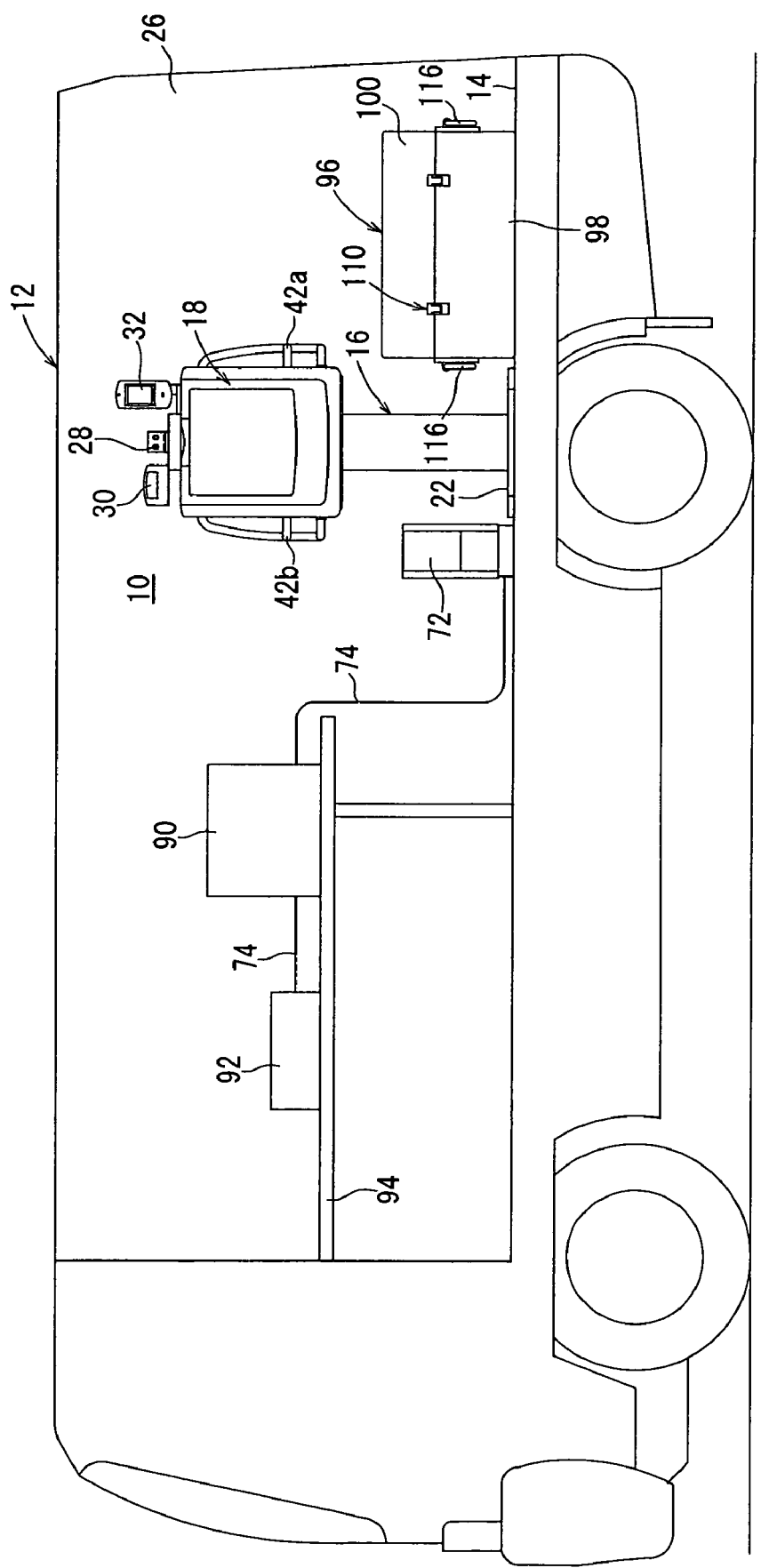
FIG. 9 is a schematic side elevational view showing a vehicle-mounted system including the image forming apparatus installed on a vehicle.

As shown in FIG. 9, a vehicle-mounted system which is installed in the compartment of the vehicle 12 includes an image processor 90 for confirming and processing image data and image information generated by the image forming apparatus 10, and a recorder 92 for saving image data and image information confirmed and processed by the image processor 90.

The image processor 90 is placed on the upper surface of a table 94 or the like and is connected to the controller 72 by a cable 74. The image processor 90 is also connected to the recorder 92 (e.g., a CD drive or a DVD drive) by a cable 74. If a printer (not shown) is connected to the image processor 90, then the printer can print image data and image information confirmed and processed by the image processor 90.

After image data and image information have been confirmed and processed by the image processor 90, these image data and image information may be saved to a recording medium (not shown) such as a CD or a DVD by the recorder 92. Then, the recording medium with the stored image data and image information may be carried out of the vehicle 12.

As shown in FIG. 9, a storage case (storage unit) 96 is mounted on the floor 14 of the vehicle 12 for storing the main unit 18 when the main unit 18 is detached from the support post 16.

Figure 8:
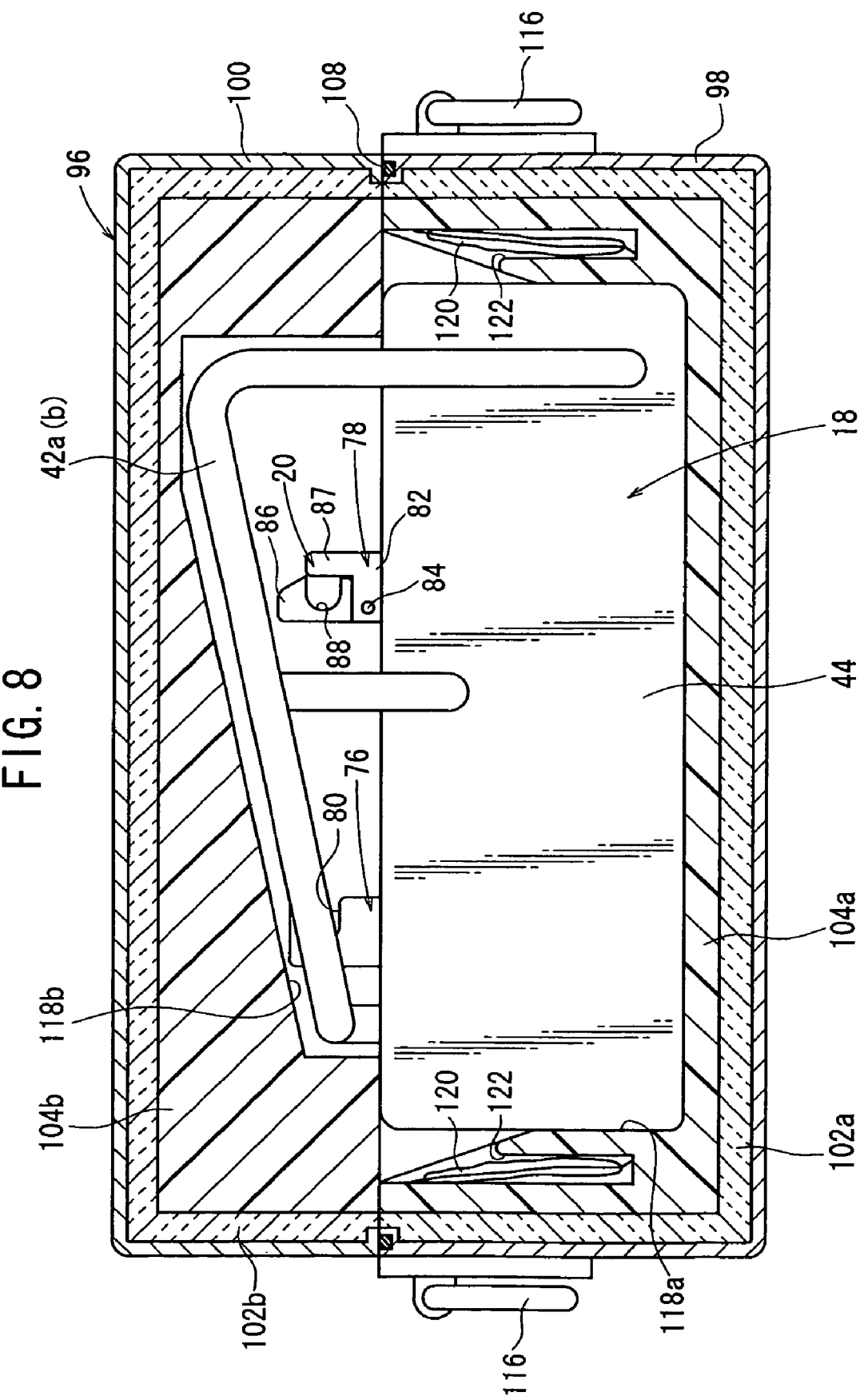
FIG. 8 is a vertical cross-sectional view of the storage case shown in FIG. 7 which stores therein the main unit and which is closed by a lid.

As shown in FIGS. 7 and 8, the storage case 96 comprises a casing 98 for storing the main unit 18 therein, a lid 100 for openably closing an upper opening of the casing 98, first and second thermal insulating members 102a, 102b covering inner wall surfaces 118a, 118b, respectively, of the casing 98 and the lid 100, and first and second damping members 104a, 104b mounted respectively in the first and second thermal insulating members 102a, 102b for protecting the main unit 18 stored in the casing 98 against vibrations, etc.

The upper opening of the casing 98 is open upwardly, and the lid 100 is angularly movably mounted on one side of the casing 98 by a plurality of hinges 106. An annular seal 108 is fitted in an annular groove defined in the upper peripheral edge of the casing 98 which is engaged by the lid 100. The annular seal 108 is made of an elastomeric material such as synthetic rubber or the like.

Lock mechanisms 110 are mounted on a side of the casing 98 which is remote from the side of the casing 98 on which the lid 100 is mounted. The lock mechanisms 110 lock the lid 100 closed on the casing 98 when the casing 98 is closed by the lid 100. Each of the lock mechanisms 110 comprises a lever 112 mounted on the side of the casing 98 and a tooth 114 positioned on the lid 100 in alignment with the lever 112. When the casing 98 is closed by the lid 100, the lever 112 is turned to bring its upper end into engagement with the tooth 114, and locked to hold the lid 100 and the case 98 tightly together.

Specifically, after the main unit 18 is housed in the casing 98, the lid 100 is turned to close the upper opening of the casing 98, and kept closed over the casing 98 by the lock mechanisms 110. The interior of the casing 98 is hermetically sealed by the annular seal 108 that is mounted in the upper peripheral edge of the casing 98 which is engaged by the lid 100.

A pair of grip handles 116 is mounted on respective opposite sides of the storage case 96 for being gripped by the carrier who carries the storage case 96.

The first thermal insulating member 102a has a substantially constant thickness and is disposed to cover the entire inner wall surface of the casing 98. The second thermal insulating member 102b is disposed to cover the entire inner wall surface of the lid 100. Therefore, the entire inner wall surfaces of the casing 98 and the lid 100 of the storage case 96 are covered with the first and second thermal insulating members 102a, 102b.

The first and second thermal insulating members 102a, 102b are made of a thermal insulating material such as glass wool, cellular plastics, or the like. The first and second thermal insulating members 102a, 102b have a thermal insulating function to prevent the heat within the storage case 96 from escaping out, thereby keeping the temperature in the storage case 96. Specifically, since the inner wall surfaces of the storage case 96 are entirely covered with the first and second thermal insulating members 102a, 102b, the temperature in the storage case 96 is maintained without being affected by the temperature outside of the storage case 96.

The first and second damping members 104a, 104b are made of an elastic material such as rubber, a foamed material, a spring member, or the like, for example, which is capable of absorbing vibrations that are applied from the vehicle 12 to the storage case 96 while the vehicle 12 is being driven. Stated otherwise, the first and second damping members 104a, 104b may be made of any materials which are capable of absorbing vibrations applied to the storage case 96 and preventing vibrations from being transmitted to the main unit 18 housed in the storage case 96.

The first damping member 104a has an outer wall surface substantially complementary in shape to the inner wall surface of the first thermal insulating member 102a, and the second damping member 104b has an outer wall surface substantially complementary in shape to the inner wall surface of the second thermal insulating member 102b. Therefore, the first damping member 104a is integrally combined with the casing 98 by the first thermal insulating member 102a, and the second damping member 104b is integrally combined with the lid 100 by the second thermal insulating member 102b.

The first damping member 104a has the inner wall surface 118a shaped to hold the exposure base 46 of the main unit 18 horizontally in a downwardly facing orientation.

The second damping member 104b has the inner wall surface 118b shaped to hold the grip bars 42a, 42b of the main unit 18 when the casing 98 is closed by the lid 100 with the main unit 18 held by the first damping member 104a. Stated otherwise, the inner wall surfaces 118a, 118b of the first and second damping members 104a, 104b are of a concave shape which is complementary to the outer profiles of the main unit 18 and the grip bars 42a, 42b at the time the lid 100 is angularly moved to-close the casing 98.

As shown in FIGS. 7 and 8, desiccants (humidity adjusters) 120 such as a deoxidizer, a silica gel, or the like for absorbing humidity in the air are disposed in the storage case 96. As shown in FIG. 8, the desiccants 120 are placed in cavities 122 defined in the inner wall surface 118a of the first damping member 104a. Since the desiccants 120 absorb humidity in the air within the storage case 96, humidity in the atmospheric air is prevented from entering the main unit 18 that is stored in the storage case 96.

When the main unit 18 is removed from the storage case 96, even if the temperature in the compartment of the vehicle 12 is higher than the temperature in the storage case 96 with the main unit 18 stored therein, since essentially no humidity is present in the main unit 18, no dew condensation occurs in the main unit 18.

The desiccants 120 may not be placed inside of the first damping member 104a, but may be positioned somewhere in the storage case 96.

The image forming apparatus 10 according to the present embodiment is basically constructed as described above. Operation and advantages of the image forming apparatus 10 will be described below.

It is assumed that the main unit 18 of the image forming apparatus 10 has been removed from the support post 16 and stored in the storage case 96 during movement of the vehicle 12. Now, a process of installing the main unit 18 on the support post 16 after the vehicle 12 has stopped will be described below.

First, the operator unlocks the lock mechanisms 110 of the storage case 96, turns open the lid 100 about the hinges 106, and removed the main unit 18 from the casing 98. As shown in FIG. 3, the operator carries the main unit 18 toward the support post 16 fixedly mounted on the floor 14 of the vehicle 12 until the mounting/dismounting mechanism 20 is brought into a position facing the mounting hole 36 in the support post 16.

Figure 4:
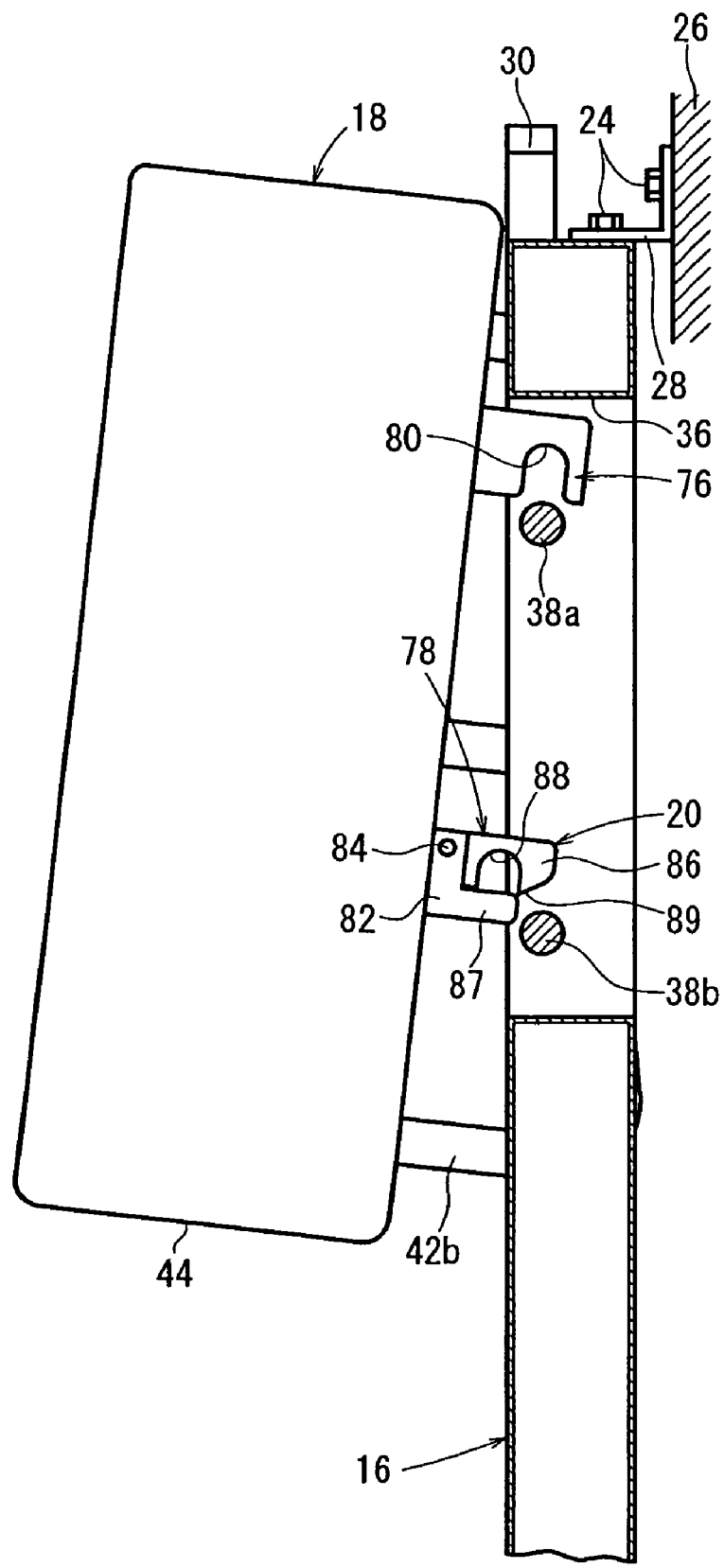
FIG. 4 is a fragmentary vertical cross-sectional view showing the manner in which first and second hooks of the main unit are inserted into a mount hole in the support post when the main unit is to be mounted on the support post shown in FIG. 3.

Then, as shown in FIG. 4, the main unit 18 is tilted at a certain angle to bring the upper end thereof closely to the support post 16, and the first and second hooks 76, 78 of the mounting/dismounting mechanism 20 are inserted into the mounting hole 36. The first hook 76 is then lowered until the shaft 38a engages in the first engaging grooves 80 (see FIG. 5). At this time, the second hook 78 abuts against an upper portion of the second shaft 38b, and is angularly moved upwardly through a certain angle against the resiliency of the spring (not shown) of the second hook 78.

Then, the lower end of the main unit 18 is tilted about the first hook 76 engaging the shaft 38a toward the support post 16 in the direction indicated by the arrow C. Upon such tilting movement of the main unit 18, the turn arms 86 of the second hook 78 are pushed upwardly by the shaft 38b until the lower slanted surfaces 89 of the turn arms 86 slide over and across the shaft 38b. After the lower slanted surfaces 89 of the turn arms 86 move beyond the shaft 38b, the turn arms 86 are pushed downwardly by the spring, and angularly moved downwardly in the direction indicated by the arrow A.

As a result, the shaft 38b engages in the second engaging grooves 88. Since the turn arms 86 are normally urged to turn clockwise downwardly in the direction indicated by the arrow A under the bias of the spring, the second hook 78 is locked against upward angular movement.

In this manner, the main unit 18 can easily be installed on the support post 16 by the shafts 38a, 38b that are positioned in the mounting hole 36 in the support post 16. The shafts 38a, 38b extend substantially parallel to each in the mounting hole 36, and the first engaging grooves 80 of the first hook 76 and the second engaging grooves 88 of the second hook 78 project substantially the same distance from the side panel of the housing 44, the main unit 18 is kept substantially parallel to the support post 16 when the shafts 38a, 38b engage in the respective first and second engaging grooves 80, 88 (see FIGS. 2 and 6).

Because the fingers 87 of the holders 82 project beneath the shaft 38b engaged by the turn arms 86, the main unit 18 fixed to the support post 16 is prevented from being displaced vertically upwardly. Therefore, when an image of the subject 34 is to be captured while the main unit 18 is being secured to the support post 16, the image can stably be captured as the main unit 18 is not displaced upwardly with respect to the support post 16.

The image forming apparatus 10 with the main unit 18 firmly installed on the support post 16 by the mounting/dismounting mechanism 20 operates as follows:

First, a process of recording radiation image information on a stimulable phosphor sheet IP will be described below. The reading/erasing unit 54 is held in a standby position at the lower end of its vertical moving stroke. The stimulable phosphor sheet IP is positioned in the solid-line position close to the exposure base 46.

The operator operates the console panel 32 (see FIG. 1) provided on the support post 16 and an unillustrated operating mechanism to vertically move the main unit 18 along the support post 16 based on a portion to be image-captured in the subject 34. The operator energizes the radiation source 48 to apply X-rays to the subject 34. The X-rays pass through the subject 34 and are applied through the phototimer 50 and the grid 52 to the stimulable phosphor sheet IP, recording radiation image information of the subject 34 on the stimulable phosphor sheet IP.

After the radiation image information is recorded on the stimulable phosphor sheet IP, the stimulable phosphor sheet IP is displaced from the solid-line position to the two-dot-and-dash-line position by a stimulable phosphor sheet moving motor (not shown). Then, the reading/erasing unit moving motor 68 is energized to cause the feed belts 66a, 66b to lift the reading/erasing unit 54, whereupon the reader 56 starts reading the radiation image information recorded on the stimulable phosphor sheet IP.

Specifically, as shown in FIG. 2, the light sources 60 of the reader 56 emit stimulating light that is applied as a line of light to the stimulable phosphor sheet IP. Upon exposure to the stimulating light, the stimulable phosphor sheet IP emits photostimulated luminescence commensurate with the radiation energy stored in the stimulable phosphor sheet IP. The emitted photostimulated luminescence is then converted by the CCD line sensors 62 that are positioned in a staggered array into an electric signal, which is processed and transmitted to the image processor 90. At this time, the reader 56 moves upwardly along the guide rails 70 to scan the stimulable phosphor sheet IP for thereby two-dimensionally reading the radiation image information that is recorded on the stimulable phosphor sheet IP over its entire area.

The reading/erasing unit 54 moves up to the upper end of its stroke, whereupon the reader 56 completes the reading of the radiation image information from the stimulable phosphor sheet IP. Thereafter, the reading/erasing unit 54 starts move downwardly, and the eraser 58 performs an erasing process. Specifically, the eraser 58 applies erasing light emitted from the light sources 64 to the stimulable phosphor sheet IP while the reading/erasing unit 54 is descending. In response to the erasing light applied to the stimulable phosphor sheet IP, the stimulable phosphor sheet IP discharges remaining radiation energy. This process continues until the reading/erasing unit 54 reaches the lower end of its stroke, whereupon the erasing of remaining radiation energy from the entire area of the stimulable phosphor sheet IP is completed.

As shown in FIG. 9, the image processor 90 confirms and processes image data and image information acquired from the stimulable phosphor sheet IP through the controller 72 connected to the image forming apparatus 10. The image data and image information may be saved to a CD or a DVD by the recorder 92, or may be printed by a printer (not shown).

After the above image forming process performed by the image forming apparatus 10 is finished, if the vehicle 12 is to be driven again, then the main unit 18 is installed on the support post 16 through the mounting/dismounting mechanism 20, and stored in the storage case 96.

Figure 5:
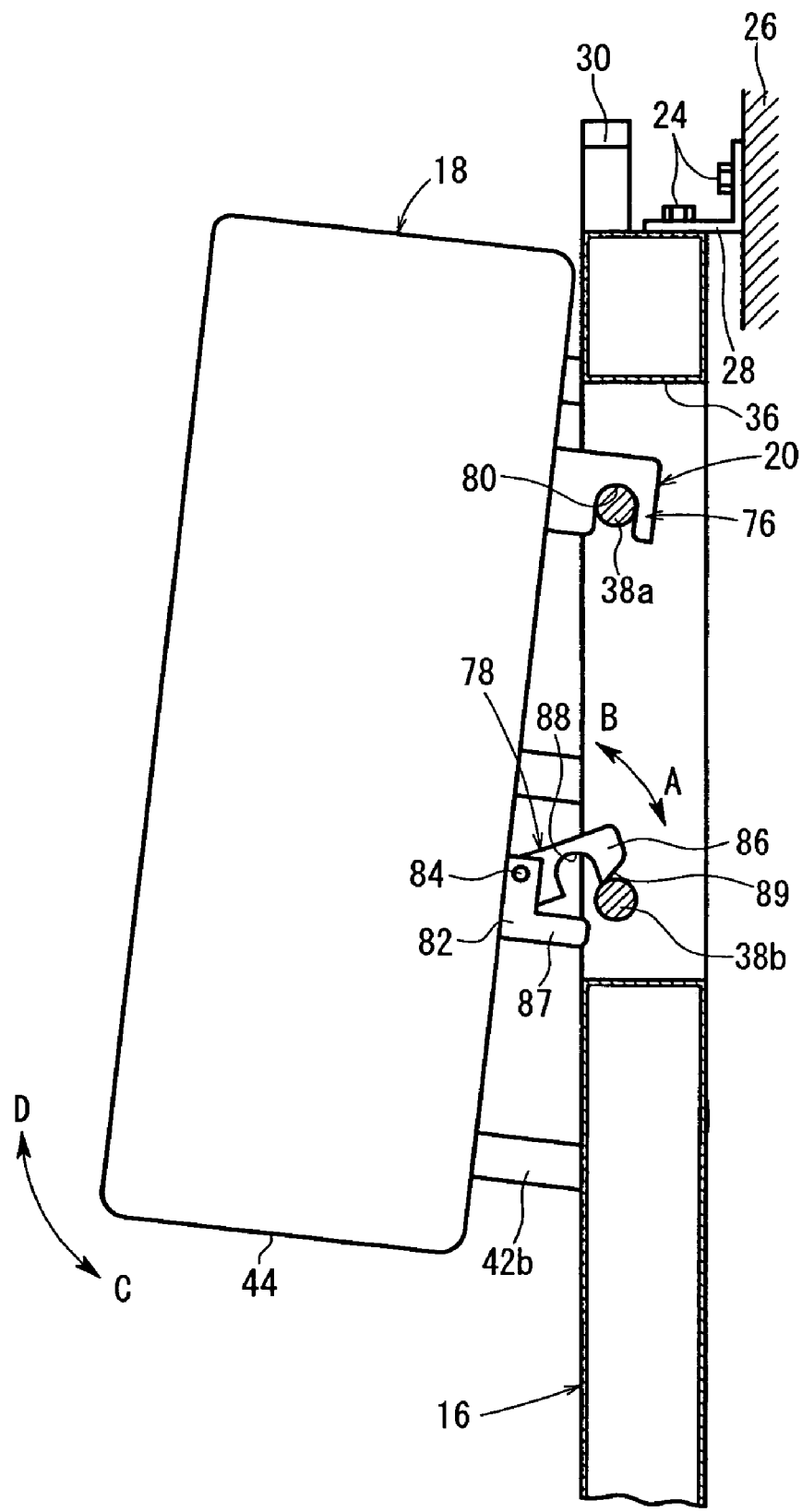
FIG. 5 is a fragmentary vertical cross-sectional view showing the manner in which the first hook shown in FIG. 4 engages a shaft in the support post and the second hook shown in FIG. 4 abuts against an upper portion of another shaft in the support post and is turned upwardly through a certain angle.
Figure 6:
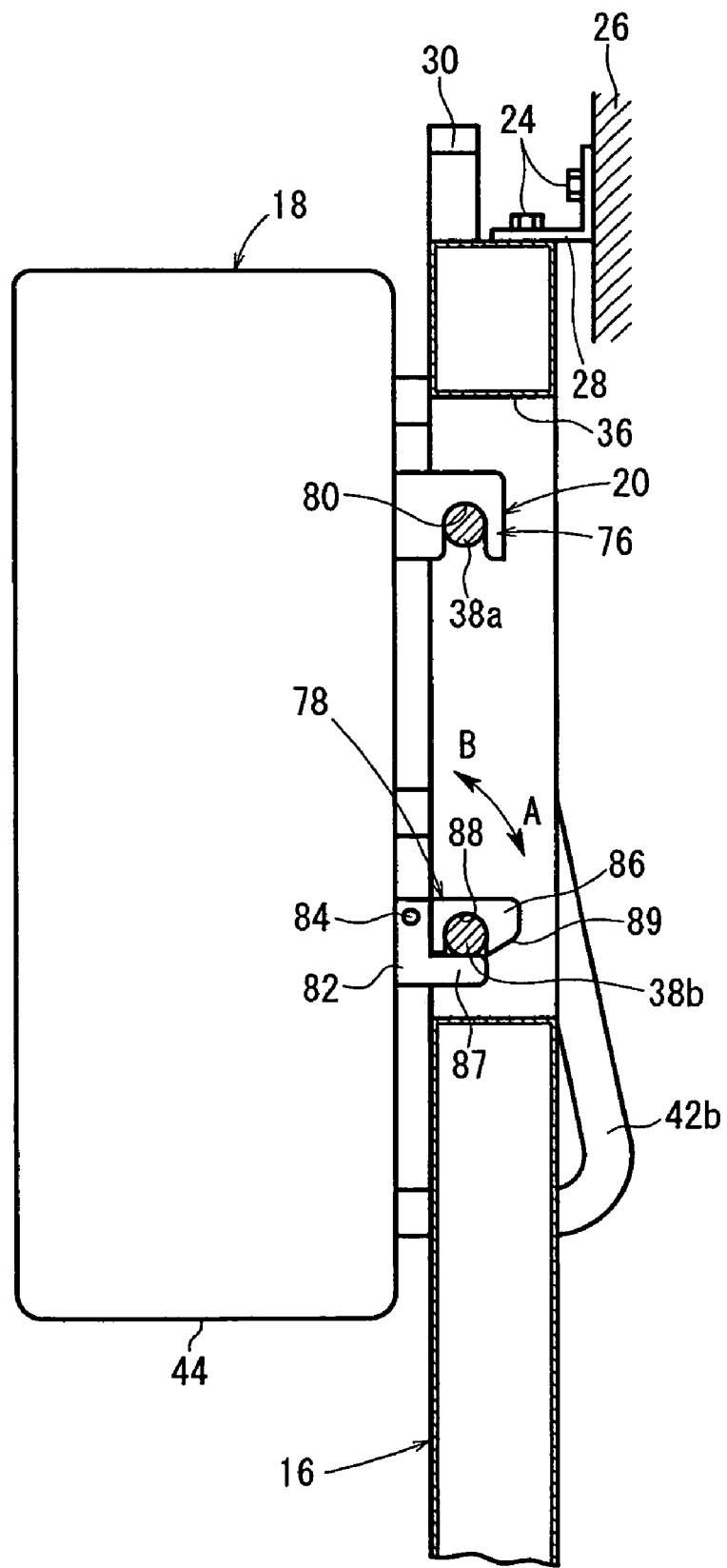
FIG. 6 is a fragmentary vertical cross-sectional view showing the manner in which the second hook shown in FIG. 5 is turned downwardly, and the first and second hooks engage the respective shafts in the support post, with the main unit fixed to the support post.

In the state shown in FIG. 6, the operator turns the turn arm 86 counterclockwise in the direction indicated by the arrow B against the resiliency of the spring (not shown) from a position near the wall 26 facing the mounting hole 36, thereby releasing the turn arm 86 of the second hook 78 from the shaft 38b. Accordingly, the second engaging groove 88 is displaced out of engagement with the shaft 38b (see FIG. 5).

The operator holds the upper end of the main unit 18, and angularly moves the lower end of the main unit 18 in the direction indicated by the arrow D in FIG. 5 away from the support post 16. After the main unit 18 is angularly moved, the main unit 18 is displaced upwardly a predetermined distance, bringing the first engaging grooves 80 of the first hook 76 out of engagement with the shaft 38a. The main unit 18 can now be freely displaced (see FIG. 4).

Then, the operator displaces the main unit 18 away from the support post 16, bringing the first and second hooks 76, 78 out of the mounting hole 36. The operator grips the grip bars 42a, 42b to carry the main unit 18 closely to the storage case 96. As shown in FIG. 8, the main unit 18 is placed into the first damping member 104a in the casing 98 with the exposure base 46 facing downwardly. When the main unit 18 is stored in the casing 98, the grip bars 42a, 42b project upwardly a certain distance from the upper surface of the casing 98.

The operator confirms that the main unit 18 is stored in the casing 98 and the main unit 18 and the grip bars 42a, 42b have their outer surfaces reliably held by the first damping member 104a. Thereafter, the operator turns the lid 100 about the hinges 106 over the casing 98 until the lid 100 abuts against the upper surface of the casing 98, thereby closing the storage case 96. The outer surfaces of the grip bars 42a, 42b which project upwardly from the upper surface of the casing 98 are held in position by the second damping member 104 disposed in the lid 100.

The levers 112 of the lock mechanisms 110 are turned into engagement with the respective teeth 114 on the lid 100, securing the lid 100 against angular movement with respect to the casing 98. The casing 98 and the lid 100 are now firmly fixed to each other, closing the storage case 96. At this time, the interior of the casing 98 and the lid 100 are hermetically sealed by the annular seal 108 positioned between the casing 98 and the lid 100.

Therefore, the main unit 18 is held in its entirety in position in the storage case 96 by the first and second damping members 104a, 104b each made of an elastic material for absorbing vibrations, and the interior of the storage case 96 is hermetically sealed by the annular seal 108.

When the vehicle 12 carrying the storage case 96 in which the main unit 18 is stored is driven, imparting vibrations from the vehicle 12 to the storage case 96, those vibrations are absorbed by the first and second damping members 104a, 104b. As a consequence, no vibrations are transmitted to the main unit 18 that is enclosed and held by the first and second damping members 104a, 104b.

The first and second damping members 104a, 104b are integrally combined with the respective first and second thermal insulating members 102a, 102b in the casing 98 and the lid 100. Therefore, the first and second damping members 104a, 104b are prevented from being displaced in the storage case 96 due to vibrations from the vehicle 12. Since the inner wall surfaces 118a, 118b of the first and second damping members 104a, 104b are shaped complementarily to the outer profiles of the main unit 18 and the grip bars 42a, 42b, the main unit 18 does not wobble within the storage case 96.

The first and second thermal insulating members 102a, 102b keep the temperature in the storage case 96 substantially constant without being affected by the temperature outside of the storage case 96.

In winter, when the main unit 18 is not in use at night, for example, it is stored in the storage case 96 placed in the compartment of the vehicle 12 which is cold, and when the main unit 18 is to be used in daytime for capturing images, the temperature in the compartment of the vehicle 12 is increased by an air conditioner or heater on the vehicle 12. In this case, inasmuch as the interior of the storage case 96 is maintained at a certain temperature by the first and second thermal insulating members 102a, 102b even at a low temperature at night, any temperature difference between the temperature in the storage case 96 and the increased temperature in the compartment of the vehicle 12 is relatively small.

Therefore, when the main unit 18 is taken from the storage case 96 into the compartment of the vehicle 12, dew condensation is prevented from occurring in the main unit 18.

The desiccants 120 disposed in the storage case 96 absorb humidity in the air within the storage case 96. Consequently, an undue amount of humidity is prevented from occurring in the main unit 18 stored in the storage case 96. Therefore, the main unit 18 is further resistant to dew condensation, since moisture in the air cannot enter the main unit 18.

With the main unit 18 stored in the storage case 96, the operator can grip the grip handles 116 of the storage case 96 to transport the main unit 18. The main unit 18 with the high-precision optical system incorporated therein can easily and safely be transported within the compartment of the vehicle 12, for example.

The image forming apparatus 10 according to the present embodiment employs the stimulable phosphor sheet IP which is incorporated in the main unit for storing part of radiation energy and emitting photostimulated luminescence commensurate with the stored level of radiation energy upon exposure to stimulating light such as a laser beam, visible light, or the like. However, the present invention is also applicable to an image forming apparatus having a solid-state sensor such as an FPD (Flat Panel Detector) capable of converting the detected energy of X-rays into an electric signal for reproducing an image.

According to the embodiment of the present invention, as described above, the main unit 18 for capturing an image of the subject 34 is detachably installed by the mounting/dismounting mechanism 20 on the support post 16 fixedly mounted in the compartment of the vehicle 12. When the vehicle 12 is to be driven, the main unit 18 can be removed from the support post 16 and stored in the storage case 96 placed in the compartment of the vehicle 12. Since the storage case 96 includes the first and second damping members 104a, 104b made of a resilient material capable of absorbing vibrations, vibrations applied from the vehicle 12 to the storage case 96 are prevented from being transmitted to the main unit 18 which is enclosed by the first and second damping members 104a, 104b.

After the vehicle 12 is driven and the main unit 18 is to be used to capture images, the main unit 18 is removed from the storage case 96 and firmly installed on the support post 16 by the mounting/dismounting mechanism 20. The main unit 18 installed on the support post 16 is now capable of capturing an image of the subject 34 as usual.

While the vehicle 12 is in motion, the main unit 18 detached from the support post 16 is stored in the storage case 96. Therefore, the main unit 18 having the optical system that is susceptible to vibrations is protected against vibrations from the vehicle 12. The image forming apparatus 10 which has the high-precision optical system that is susceptible to vibrations can be carried on the vehicle 12.

For installing the main unit 18 on the support post 16, the first and second hooks 76, 78 of the mounting/dismounting mechanism 20 are brought into engagement with the respective shafts 38a, 48b in the support post 16. The main unit 18 can thus easily be installed on the support post 16. The main unit 18 can also easily be detached from the support post 16 simply by releasing the first and second hooks 76, 78 from the respective shafts 38a, 48b in the support post 16.

Therefore, the operator can easily install the main unit 18 on and remove the main unit 18 from the support post 16 highly efficiently within a short period of time.

Furthermore, the inner wall surfaces 118a, 118b of the first and second damping members 104a, 104b are shaped complementarily to the outer profiles of the main unit 18 and the grip bars 42a, 42b to firmly hold the main unit 18 and the grip bars 42a, 42b. Accordingly, the main unit 18 stored in the storage unit 96 is prevented from wobbling or being displaced in the storage case 96 due to vibrations from the vehicle 12.

Moreover, the first and second thermal insulating members 102a, 102b made of a thermal insulating material for maintaining a predetermined temperature are disposed in the storage case 96. The temperature in the storage case 96 which is storing the main unit 18 is not unduly affected by changes in the temperature in the compartment of the vehicle 12, and protected against undue temperature changes even though the main unit 18 is placed in the compartment of the vehicle 12 whose temperature suffers relatively large changes.

Inasmuch as the interior of the storage case 96 is kept at a certain temperature, even if the temperature in the compartment of the vehicle 12 undergoes a sharp rise, any temperature difference between the temperature in the compartment of the vehicle 12 and the temperature of the main unit 18 is minimized, preventing dew condensation from being developed in the main unit 18.

The storage case 96 has a heating device (not shown) such as a heater or the like which can be heated to a predetermined temperature. If the main unit 18 stored in the storage case 96 is to be stored or used at low temperatures in cold climate or winter, the heating device is energized to keep the interior of the storage case 96 at a desired temperature.

Therefore, even when the compartment of the vehicle 12 is heated to a certain temperature by the air conditioner or heater on the vehicle 12, the temperature in the storage case 96 can be made substantially equal to the temperature in the compartment of the vehicle 12. Consequently, dew concentration is prevented from occurring in the main unit 18 when the main unit 18 is removed from the storage case 96.

When the main unit 18 is removed from the support post 16 and stored in the storage-case 96, the main unit 18 with the high-precision optical system can easily be transported in the compartment of the vehicle 12 by the operator.

In the above description, the main unit 18 is firmly installed on the support post 16 by engaging the shafts 38a, 38b in the mounting hole 36 in the support post 16 through the mounting/dismounting mechanism 20. However, the mounting hole 36 and the shaft 38a, 38b may be provided in the wall 26 of the vehicle 12, and the main unit 18 may be removably installed on the wall 26 of the vehicle 12 by the mounting/dismounting mechanism 20. According to such a modification, since the support post 16 for supporting the main unit 18 is dispensed with, a limited space in the compartment of the vehicle 12 can effectively be utilized.

The mounting/dismounting mechanism 20 by which the main unit 18 is detachably installed on the support post 16 or the wall 26 of the vehicle 12 is not limited to the first hook 76 and the second hook 78 for engaging the shafts 38a, 38b. Instead, the main unit 18 may be detachably installed on the support post 16 or the wall 26 of the vehicle 12 under magnetic forces by a magnetic fixing mechanism such as a magnetic clamp or the like, or by a lock pin which is displaceable by the turning movement of a lever or the like, or by screws. Any fixing mechanisms may be used insofar as they can detachably install the main unit 18 on the support post 16 or the wall 26 of the vehicle 12.

Although certain preferred embodiments of the present invention have been shown and described in detail, it should be understood that various changes and modifications may be made therein without departing from the scope of the appended claims.

What is claimed is:

1. An image forming apparatus comprising:
   an exposure unit adapted to be mounted in a compartment of a vehicle to capture a radiation image of a subject irradiated by a radiation source;
   a mount adapted to be fixedly mounted in the compartment of the vehicle, for holding said exposure unit; and
   a mounting/dismounting mechanism for detachably installing said exposure unit on said mount, wherein the exposure unit is mounted to the fixedly mounted mount during exposure operation and is removably detached from the fixedly mounted mount during storage.

2. An image forming apparatus comprising:

an exposure unit adapted to be mounted in a compartment of a vehicle to capture a radiation image of a subject irradiated by a radiation source;

a mount adapted to be fixedly mounted in the compartment of the vehicle, for holding said exposure unit; and a mounting/dismounting mechanism for detachably installing said exposure unit on said mount, wherein said mounting/dismounting mechanism comprises a first engaging member mounted on a surface of said exposure unit which faces said mount, and a second engaging member angularly movably supported on said exposure unit, and said mount has a first engaging element and a second engaging element, and wherein when said exposure unit is to be installed on said mount, said first engaging member engages said first engaging element of said mount and said second engaging member engages said second engaging element of said mount.

3. An image forming apparatus according to claim 2, wherein said first engaging member and said second engaging member have a first engaging groove and a second engaging groove, respectively, defined therein, said first engaging groove and said second engaging groove being spaced from each other by a distance which is substantially the same as a distance between said first engaging element and said second engaging element.

4. An image forming apparatus according to claim 2, wherein said second engaging member has a slanted surface which is slanted at a predetermined angle on a lower surface thereof which is closer to said mount than said second engaging groove.

5. An image forming apparatus comprising:

an exposure unit adapted to be mounted in a compartment of a vehicle to capture a radiation image of a subject irradiated by a radiation source;

a mount adapted to be fixedly mounted in the compartment of the vehicle, for holding said exposure unit;

a mounting/dismounting mechanism for detachably installing said exposure unit on said mount; and a storage unit adapted to be disposed in the compartment of the vehicle, for storing said exposure unit when the exposure unit is detached from said mount;

said storage unit including a casing for storing said exposure unit in an opening of said casing, and a lid for closing said opening.

6. An image forming apparatus according to claim 5, wherein said storage unit includes a damping member disposed therein for preventing vibrations applied by said vehicle from being transmitted to said exposure unit.

7. An image forming apparatus according to claim 6, wherein said damping member is of a concave shape complementary to a profile of said exposure unit to be enclosed by said damping members.

8. An image forming apparatus according to claim 5, wherein said storage unit includes a thermally insulating member disposed therein for maintaining a temperature in said storage unit.

9. An image forming apparatus according to claim 8, wherein said storage unit includes a desiccant disposed therein for absorbing humidity in said storage unit.

10. An image forming apparatus according to claim 5, wherein said storage unit includes a thermally insulating member disposed on and along an inner wall surface of said storage unit, for maintaining a temperature in said storage unit, and a damping member disposed on an inner wall surface of said thermally insulating member, for preventing vibrations applied by said vehicle from being transmitted to said exposure unit.

11. An image forming apparatus according to claim 5, further comprising:

a seal of an elastomeric material disposed between respective abutting surfaces of said casing and said lid.

12. A method of transporting an image forming apparatus including an exposure unit adapted to be mounted in a compartment of a vehicle to capture a radiation image of a subject irradiated by a radiation source, a mount adapted to be fixedly mounted in the compartment of the vehicle for holding said exposure unit, and a mounting/dismounting mechanism for detachably installing said exposure unit on said mount, said method comprising the steps of:

detaching said exposure unit from the mount fixedly mounted in the compartment of the vehicle through said mounting/dismounting mechanism;

storing said exposure unit in a storage unit disposed in the compartment of the vehicle, said storage unit including a damping member for preventing vibrations applied by said vehicle from being transmitted to said exposure unit, and a thermally insulating member for maintaining a temperature in said storage unit;

closing said storage unit with a lid; and carrying said exposure unit stored in said storage unit.

13. An image forming apparatus comprising:

an exposure unit adapted to be mounted in a compartment of a vehicle to capture a radiation image of a subject irradiated by a radiation source;

a mount adapted to be fixedly mounted in the compartment of the vehicle, for holding said exposure unit; and a mounting/dismounting mechanism for detachably installing said exposure unit on said mount, wherein the exposure unit includes a scanning unit and houses a storage medium, and wherein the scanning unit is movable in relation to the storage medium which stores the captured radiation image of the subject, wherein the storage medium comprises a stimulable phosphor sheet, and the scanning unit traverses a dimension of the stimulable phosphor sheet to read out the captured radiation image.

* * * * *